US008516497B2

(12) United States Patent
Ma et al.

(10) Patent No.: US 8,516,497 B2
(45) Date of Patent: Aug. 20, 2013

(54) ARCHITECT FOR PROCESS SHARING BETWEEN INDEPENDENT SYSTEMS/APPLICATIONS IN MEDICAL IMAGING

(75) Inventors: Feng Ma, Pennington, NJ (US); Qian Jianzhong, Princeton Junction, NJ (US); Guo-Qing Wei, Plainsboro, NJ (US); Cheng-Chung Liang, West Windsor, NJ (US); Xiaolan Zeng, Princeton, NJ (US); Li Fan, Belle Mead, NJ (US); Hong Chen, Plainsboro, NJ (US)

(73) Assignee: Edda Technology, Inc., Princeton Junction, NJ (US)

( * ) Notice: Subject to any disclaimer, the term of this patent is extended or adjusted under 35 U.S.C. 154(b) by 910 days.

(21) Appl. No.: 12/209,667

(22) Filed: Sep. 12, 2008

(65) Prior Publication Data
US 2009/0077157 A1 Mar. 19, 2009

Related U.S. Application Data
(60) Provisional application No. 60/972,403, filed on Sep. 14, 2007.

(51) Int. Cl.
*G06F 13/00* (2006.01)
(52) U.S. Cl.
USPC .......................... 719/312; 719/318; 719/328
(58) Field of Classification Search
USPC .......................................... 719/312, 318, 328
See application file for complete search history.

(56) References Cited

U.S. PATENT DOCUMENTS

| 2002/0180798 | A1* | 12/2002 | Poor et al. ..................... 345/781 |
| 2005/0125486 | A1* | 6/2005 | Chrysanthakopoulos et al. .............................. 709/201 |
| 2005/0144482 | A1* | 6/2005 | Anuszewski .................. 713/201 |
| 2006/0236328 | A1 | 10/2006 | DeWitt |
| 2007/0143342 | A1* | 6/2007 | VanNostrand ............. 707/104.1 |
| 2007/0192354 | A1 | 8/2007 | Wei et al. |

FOREIGN PATENT DOCUMENTS
WO 2007-026318 3/2007

OTHER PUBLICATIONS

International Search Report and Written Opinion of the International Searching Authority issued in corresponding International Patent Application No. PCT/08/76239, dated Nov. 18, 2008.
European Search Report corresponding to European Serial No. 08830188.2 dated Mar. 18, 2013.

* cited by examiner

*Primary Examiner* — Andy Ho
(74) *Attorney, Agent, or Firm* — Dentons US LLP

(57) ABSTRACT

Method and system for process sharing in a medical imaging system are disclosed. A first application system is provided capable of processing data within a second application system. A process sharing system residing outside of the second application system is configured for enabling process sharing of the first application system within the second application system. The first application system comprises a front-end unit that is made operable within the second application system by a process launcher upon occurrence of an event to facilitate processing of data accessible from the second application system through communication with the process sharing system via a pre-defined interface. The process launcher is generated by the process sharing system and deployed on the second application system.

23 Claims, 11 Drawing Sheets

ARCHITECT FOR PROCESS SHARING BETWEEN INDEPENDENT SYSTEMS/APPLICATIONS IN MEDICAL IMAGING

RELATED APPLICATION

The present invention claims priority of provisional patent application No. 60/972,403 filed Sep. 14, 2007, the contents of which are incorporated herein in their entirety.

BACKGROUND

1. Technical Field

The present teaching relates to process sharing between independent medical imaging systems.

2. Discussion of Related Art

In medical imaging, patient data may be processed and viewed with different applications. There is a need to share processes among such independent applications on the same computer to ensure a smooth and integrated workflow. For example, within one application, a user may want to use another dedicated application to further analyze patient data. To achieve that, conventionally, code level integration between the different applications is a commonly used resolution. For example, a dedicated Computer-Aided Detection (CAD) system is designed to identify locations of suspicious regions and provide interactive tools to evaluate the regions of interest (ROI) in various ways. A Picture Archiving and Communication System (PACS) is a dedicated platform to store and view medical images. One way to enable special purpose applications, such as the CAD systems or 3D visualization systems on PACS system is to conduct code level integration between the PACS and the application systems. For example, a designated button may be placed in PACS graphics user interface (GUI) and a click of the button may activate the CAD application to analyze the patient data with tools offered by the CAD system. However, code level integration between independent systems solves the problem only to some extent. Considering the fact that there are numerous special purpose applications and PACS systems on the market, integrating these systems requires tremendous amount of engineering work from each vendor. Furthermore, release of a new version of software from one vendor may need additional validation efforts from the other vendor and may inevitably lengthen the release procedure. This may impose a significant burden on application vendors and PACS vendors. In addition, it makes it much harder for users to promptly utilize latest technologies because newly developed special purpose applications or PACS systems may have to first undergo extensive and continuous integration efforts in order to enable users to enjoy the integrated benefits. With more application vendors and more PACS vendors emerging, the situation become more and more infeasible. The underlying reason for this chaos is the mutual dependence created by the code level integration.

Given this situation, a scalable architecture that enables inter-operability among independent medical systems is needed.

BRIEF DESCRIPTION OF THE DRAWINGS

The inventions claimed and/or described herein are further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

DETAILED DESCRIPTION

Figure 1:
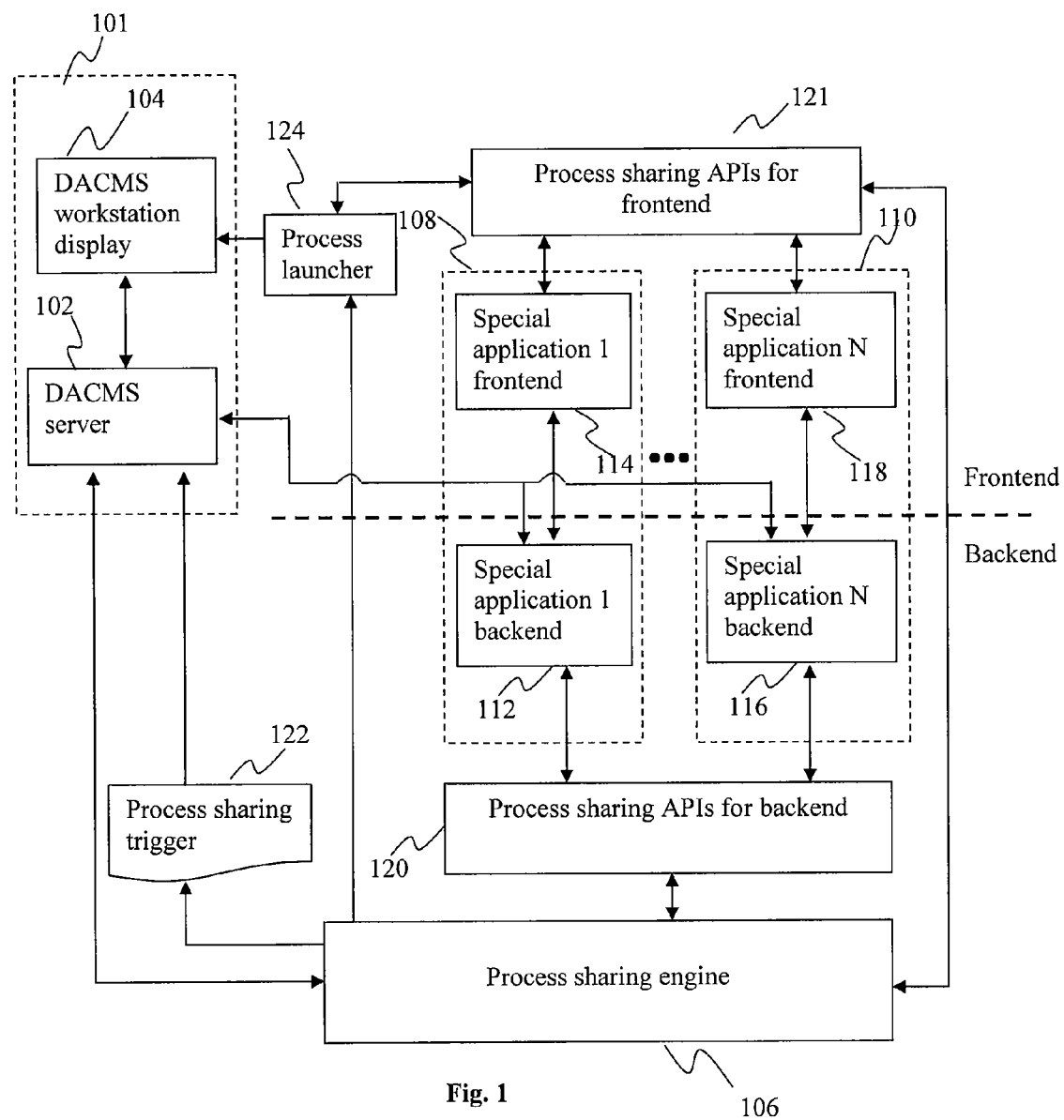
FIG. 1 depict an exemplary system diagram for a process sharing engine, according to an embodiment of the present teaching.

FIG. 1 shows an exemplary system diagram of a process sharing engine system, according to an embodiment of the present teaching. The system comprises a Data Archiving, Communication, and Manipulation System (DACMS) system 101, a plurality of special purpose applications (application 108, ..., and application 110), a process sharing engine 106, and a set of process sharing Application Program Interfaces (APIs) for backend 120 and front-end 121, designed for facilitate communications between the special purpose applications and other components of the system configuration such as the process sharing engine 106. The DACMS system 101 may include a DACMS server 102 and one or more DACMS review workstations 104. An example of a DACMS system is a PACS system. The process sharing engine 106 is designed to enable multiple special purpose applications to share processes and communicate with DACMS system 101.

Each of the special purpose applications 108, ..., and 110 may have certain configurations. For example, in some embodiments, each special purpose software application may be decomposed into corresponding backend processing unit and front-end processing unit, shown in FIG. 1 as backend processing units 112, ..., 116 and front-end units 114, ..., 118, respectively. A special purpose application may also include only a frontend application unit without a backend processing unit. The special purpose applications 108, ..., 110 may communicate with the DACMS system 101 via different routes. For instance, a special purpose application (e.g., 108) may interface with the DACMS system directly via its backend 112 to, e.g., obtain patient data. Upon receiving data from the DACMS system, the special purpose applications may then perform processing thereof via the backend units 112, ..., 116. A special purpose application may also interact with the DACMS system through the processing sharing engine via processing sharing APIs for either the front-end or the backend, as shown in FIG. 1. In this manner, the process sharing engine 106 may obtain patient data from the DACMS server 101 and then transfer the patient data to the backend units 112, ..., 116 via the processing sharing APIs for backend 120 for processing.

Through the processing sharing APIs for backend 120, the process sharing engine 106 may also monitor the status of the backend processing units 112, ..., 116. After the completion of the backend processing on certain patient data by the backend units 112, ..., 116, the process sharing engine 106 may generate one or more process sharing triggers 122 based on a combination of the patient data (and/or its processed result) and certain information associated with the corresponding special purpose application used to process the patient data. In some embodiments, such a trigger may contain the patient data and its processed result and a unique ID identifying the special purpose application used to perform the processing. In some embodiments, the trigger data may also include a portion of the special purpose application used in processing the patient data. In some embodiments, the trigger data may include directly a full version of the special purpose application. The trigger data is than sent to the DACMS server 102. Such transmission may be performed utilizing some standard protocol, e.g., DICOM.

Methods and system to generate process sharing trigger 122, to deploy process launcher 124 on the DACMS system 101, and to launch front-ends of the special purpose software applications 114, ..., 118 within the DACMS system 101 were described in previous patent applications, U.S. patent application Ser. No. 11/647,597, by Guo-Qing Wei, Cheng-Chung Liang, Feng Ma, Li Fan, Jianzhong Qian, Xiaolan Zeng, entitled "Methods for process sharing among independent systems/applications via data encapsulation in medical imaging"; as well as U.S. patent application No. 60/792,344, by Jianzhong Qian, Feng Ma, Guo-Qing Wei, Cheng-Chung Liang, Li Fan, Xiaolan Zeng, Tim Ketchmark, entitled "Methods for enabling an application within another independent system/application via data encapsulation in medical imaging". They are hereby incorporated by reference.

To achieve process sharing, the process sharing engine 106 may deploy a process launcher 124 at a DACMS's review workstation 104. The process launcher 124 may include separate components such as a trigger response unit and a launcher (described in detail in the incorporated prior applications). The deployed process launcher resides on a DACMS workstation and monitor the incoming triggers loaded on the workstation and respond to such triggers by launching corresponding front-end of a special purpose application on the workstation to allow process sharing of the special purpose application within the DACMS environment.

In operation, responding to a user's selection, a DACMS workstation may load the patient data that includes a trigger, e.g., the process sharing trigger 122, encoded with information related to the special purpose application. The trigger may be displayed on the workstation display so that the user can select when needed. If the user further selects the trigger, a trigger response unit included in the process launcher 124 detects the presence of the trigger and then decodes the trigger to extract information associated with the special purpose application. Based on such information, the frontends of the special purpose software application(s) 114, ..., 118 may be launched, on the review workstation 104 within the DACMS system. The application frontend units 114, ... 118 may also communicate with the process sharing engine 106 through the process sharing APIs for the frontend 121 to obtain processed results for the loaded patient data. Through such APIs between the special purpose applications and the process sharing engine 106, the special purpose applications 108, ..., 110 and the DACMS system 101 may communicate and cooperate on the same patient data without code level integration.

According to the present teaching, the process sharing engine 106 is a platform having support hardware and software. The backend units 112, ... 116 of the special purpose applications may be installed on the a computer where the process sharing engine machine 106 resides. The backend units 112, ..., 116 may also be installed on a separate computer. In that case, the backend units 112, ..., 116 may communicate with the processing sharing engine 106 through a computer network. Such a network may be of any form such as wired network, wireless network, the Internet, an intranet, a proprietary network, a virtual network, a local area network (LAN), or a wide area network (WAN), or any combination thereof.

The process launcher 124 may be a software component of the process sharing engine 106 and may be deployed to run on a DACMS review workstation 104. It may also be installed directly on the DACMS review workstation 104. The frontends of the special purpose software applications 114, ..., 118 may also be software components residing on the same computer as the processing sharing engine 106. These frontends of the special purpose software applications may also be installed directly on the DACMS review workstation 104. The application frontend units 114, ..., 118 may be launched by the process launcher 124 on the DACMS review workstation 104, upon activated by the process sharing trigger 122. The process sharing engine 106, the DACMS system 101, and the special applications 108, ..., 110 may be connected through a network, which can be of any form such as wired network, wireless network, the Internet, an intranet, a proprietary network, a virtual network, a local area network (LAN), or a wide area network (WAN), or any combination thereof.

Figure 2:
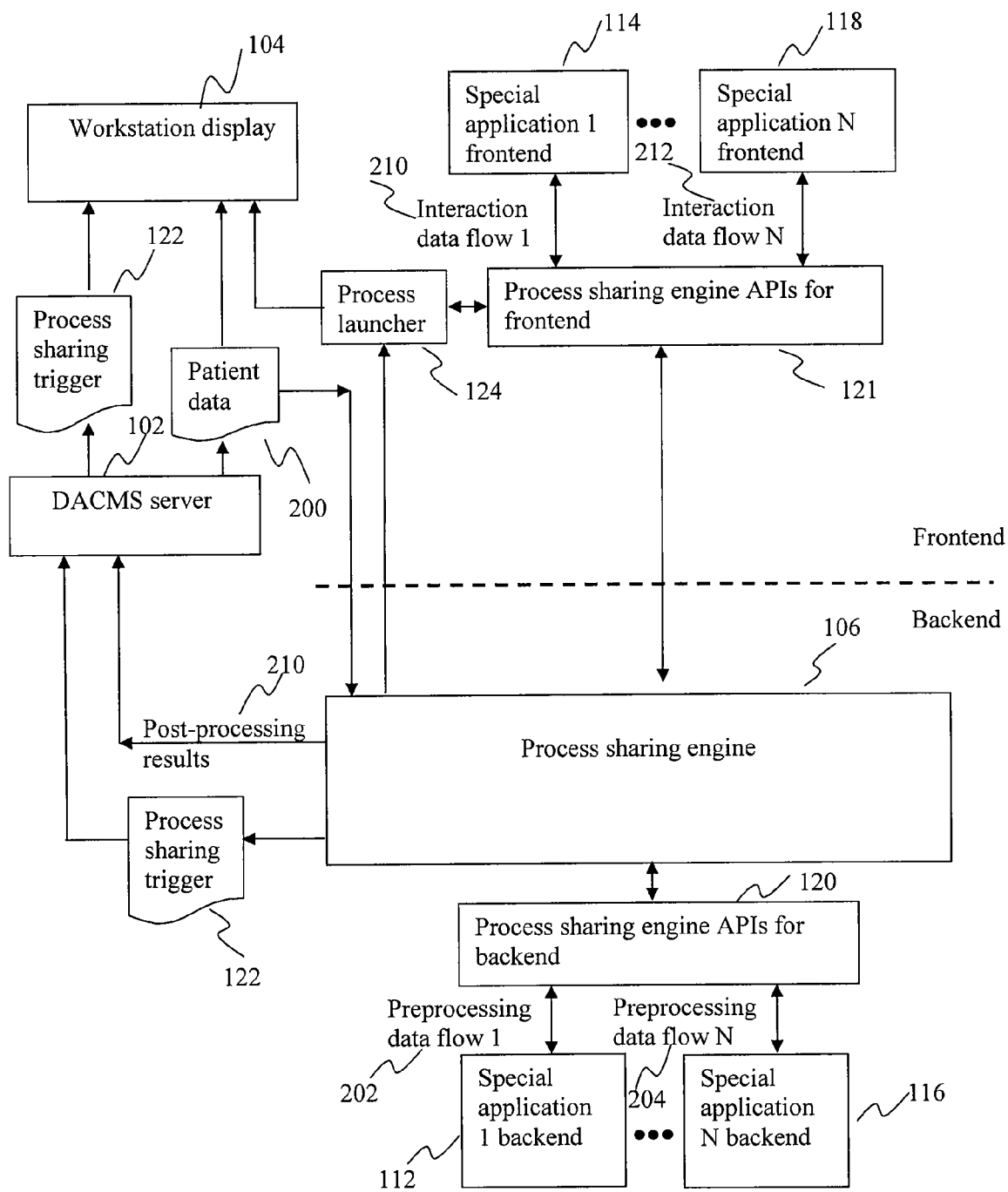
FIG. 2 shows a detailed exemplary system diagram of a process sharing engine, according to an embodiment of the present teaching.

FIG. 2 is a detailed system diagram of the process sharing engine, according to an embodiment of the present teaching. In this diagram, the process sharing engine 106 receives patient data 200 from the DCMS server 102 based on some standard, e.g., the DICOM standard. Through process sharing engine API for backend 120, the patient data may be passed to the backend units 112, ..., 116. The backend processing units may then process the patient data and send status information to the process sharing engine 106. The process sharing engine 106 may generate the trigger data 122 based on the patient data and/or its processed result as well as information associated with the special purpose application used to perform the processing. Such trigger data 122 are then sent to the DACMS server 102. Any data stored on the DACMS server 102 can be retrieved for viewing or processing by a DACMS workstation. As discussed herein, when a user selects to view data associated with a certain patient, information related to the selected patient can be loaded to the DACMS workstation and such information may include the trigger data 122. When the trigger is selected by the user, the process launcher 124 launches the corresponding front-end of the special purpose application used to process the loaded patient data on the workstation, making it available for further processing the same patient data.

The application frontend 114, . . . , 118 may receive the preprocessing results 202 and 204 from the backend of the process sharing engine 106 or from the backend units 112, . . . 116 through the frontend APIs 121. Post-processing results 210 and 212 may be generated by application frontends 114, . . . , 118 and sent back to the process sharing engine 106 or the corresponding backend units 112, . . . , 116. The process sharing engine 106 and the backend units 112, . . . , 116 may subsequently send selected post-processing results 210 to DACMS server 102.

Figure 3A:
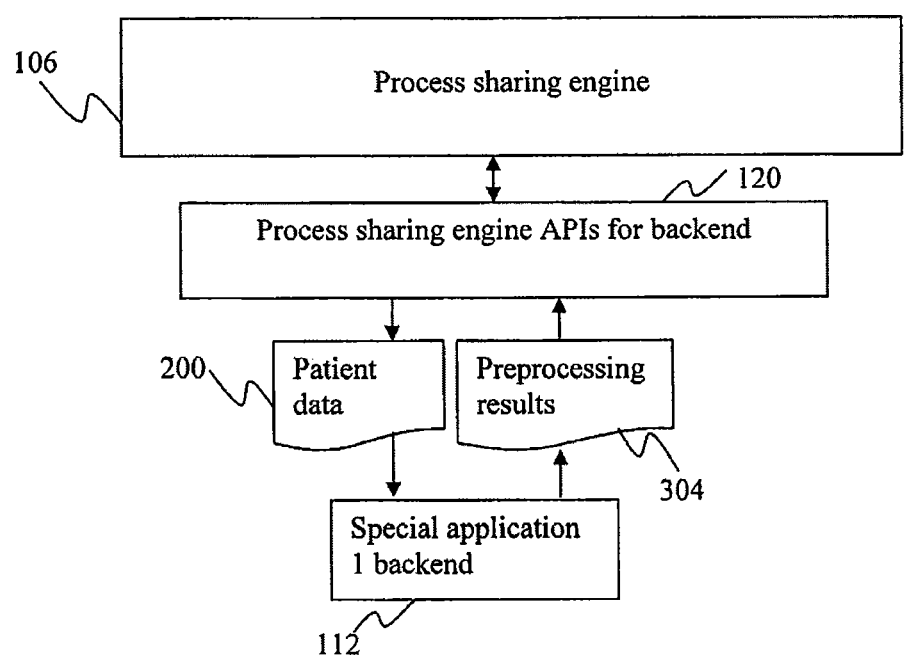
FIG. 3a shows an exemplary data flow between a process sharing engine and the backend of a special application, according to an embodiment of the present teaching.

FIG. 3*a* is an exemplary diagram of the API-based communication between the process sharing engine 106 and the application backend unit 112. In this diagram, patient data 200 is sent from the process sharing engine 106 to special application backend 112, through the process sharing engine API for backend 120. The process sharing engine 106 may obtain such patient data from the DACMS server 102. Upon completion of the processing of the data by the backend unit, the backend unit sends the preprocessing results 304 to the process sharing engine 106 through the process sharing engine API for backend 120.

Figure 3B:
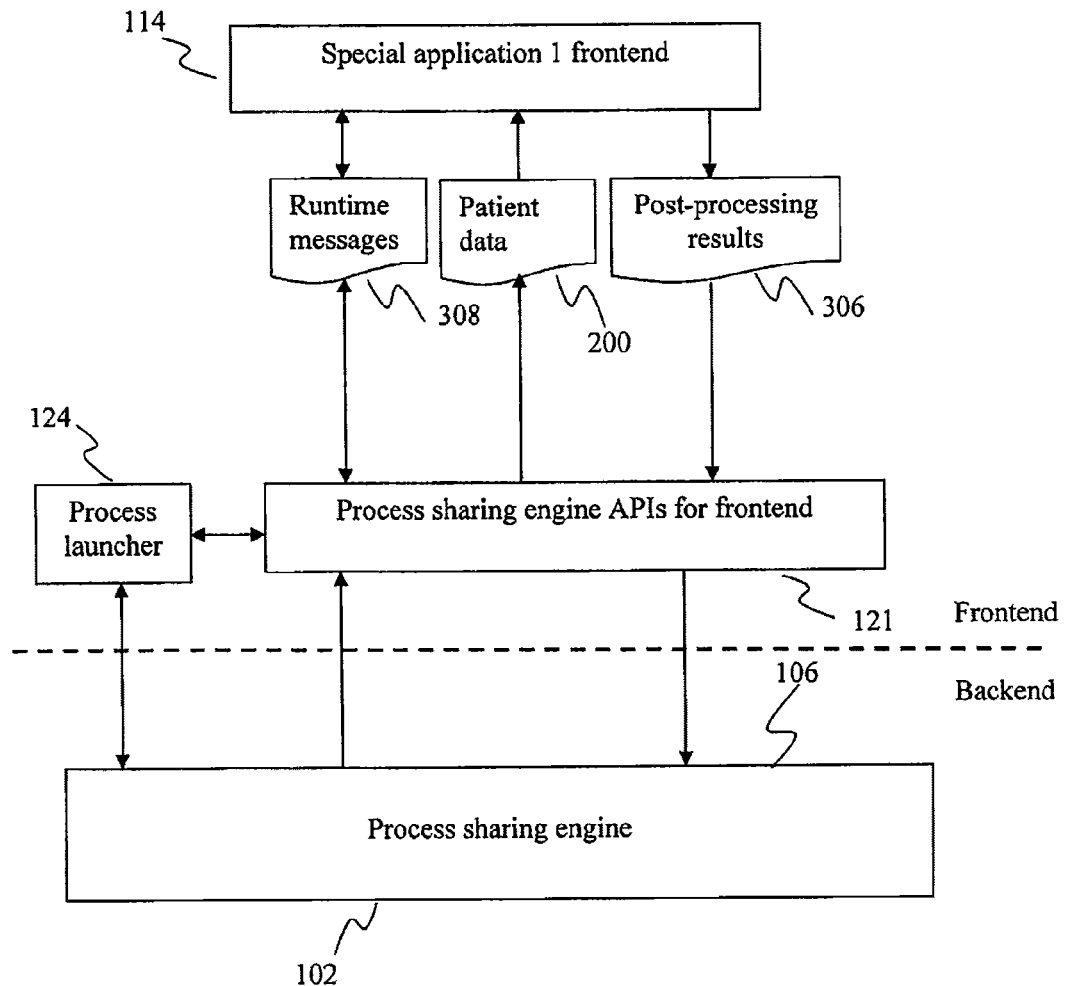
FIG. 3b shows an exemplary data flow between a process sharing engine and the front-end of a special application, according to an embodiment of the present teaching.

FIG. 3*b* is an exemplary diagram of the API-based communication between process sharing engine 106 and the application front-end unit 114. Patient data 200 may be sent to special purpose application 1's front-end 114 from the process sharing engine 106, through the process sharing engine API for frontend 121 (see FIG. 2). Runtime messages 308 may be sent among the special application frontend 114, the process sharing engine 106, and the process launcher 124, to exchange status information of the frontend with the process launcher and/or to request preprocessing result from the process sharing engine. The status information of the frontend may include, but not limited to, whether the GUI is shown or closed, the display position of the GUI etc. Post-processing results 306 generated by the special application frontend 114 may be sent to the process sharing engine 106 through the process sharing engine API for frontend 121. After the process sharing engine 106 received the post processing results 306, it may forward the results 306 to DACMS server 102.

Figure 3C:
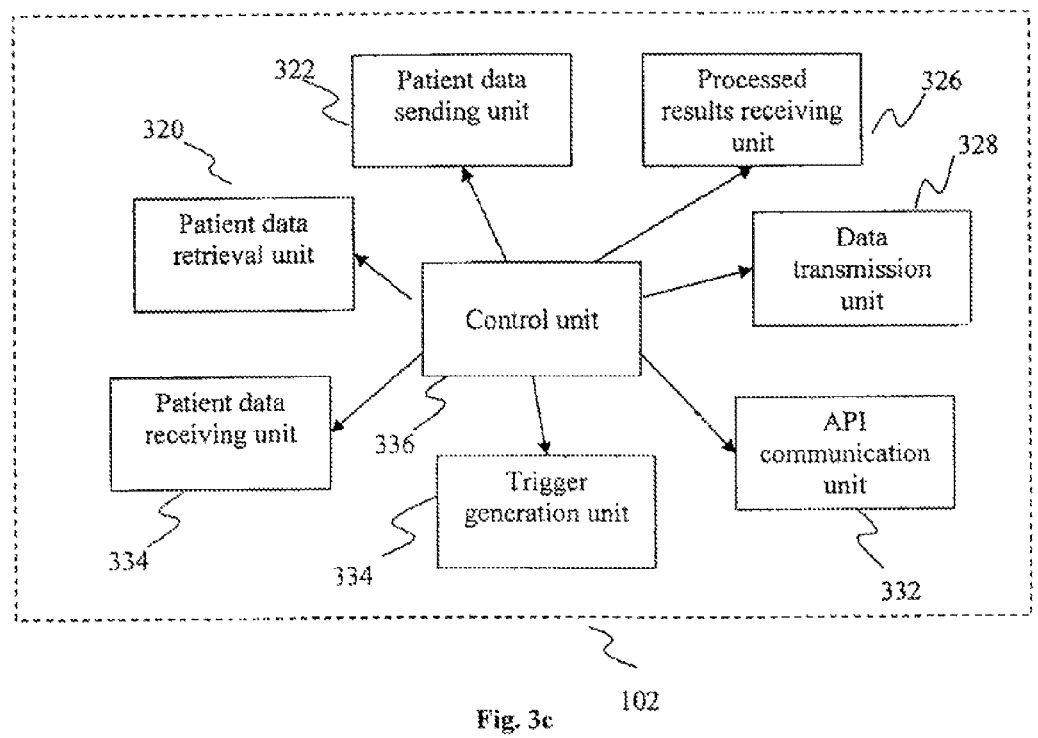
FIG. 3c shows an exemplary diagram for a process sharing engine, according to an embodiment of the present teaching.

FIG. 3*c* illustrates an exemplary diagram for the processing sharing engine 102. The process sharing engine 102 comprises a trigger data generation unit 334, a data transmission unit 328, which sends both trigger data and processed result data to DACMS server 102, and a processed results receiving unit 326 for obtaining processed results from backend units of the special applications. Optionally, the processing sharing engine 102 may additionally comprise a patient data retrieval unit 320 for requesting patient data from DACMS server 102, a patient data sending unit 322 for sending retrieved patient data to special application backend units for data processing. Furthermore, the process sharing engine may also comprise a control unit 336 for coordinating different tasks, and an API communication unit 332 responsible for communicating with the special application frontend and backend units.

Figure 3D:
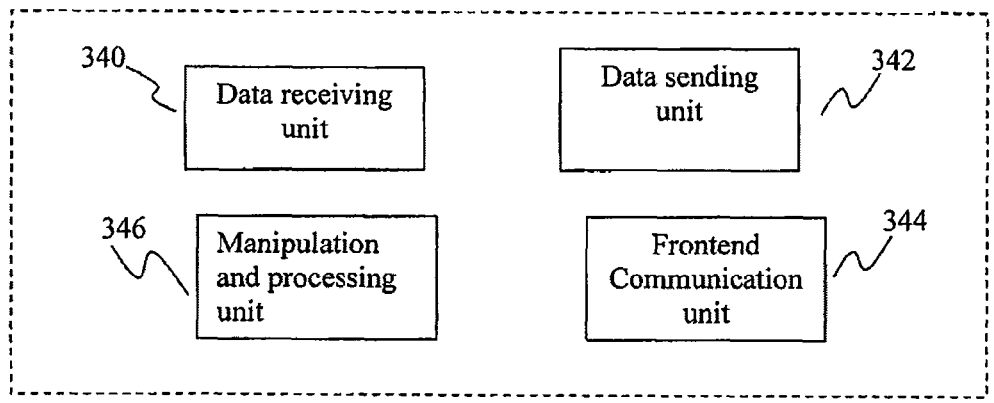
FIG. 3d shows an exemplary diagram of components for a frontend unit, according to an embodiment of the present teaching.

FIG. 3*d* is an exemplar diagram of the frontend unit of a special application. A frontend unit may comprise a data receiving unit 340 for receiving patient data from the processing sliming engine 106 and/or from the backend of the special application, a manipulation and processing unit 346 for processing the received patient data, a data sending unit 342 for sending post-processed results to the processing sharing engine 106 and/or a corresponding backend unit. A frontend unit may further includes a communication unit 344 for communicating with the process sharing engine 106 or a backend unit.

Figure 3E:
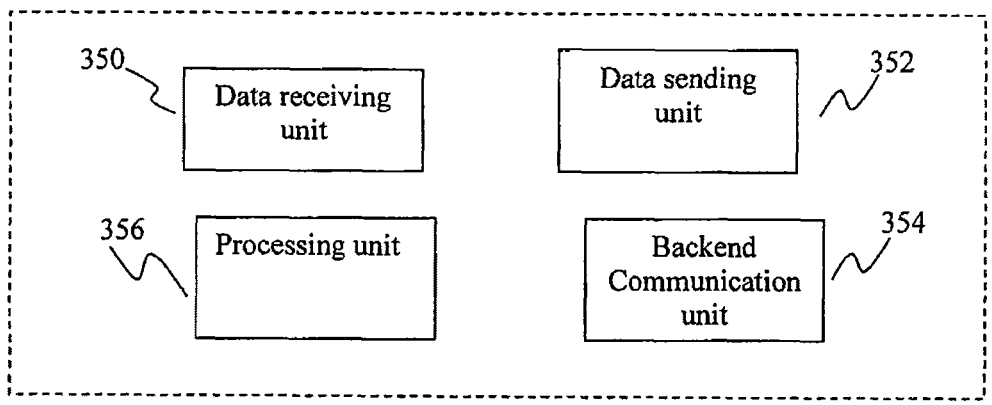
FIG. 3e shows an exemplary diagram for components of a backend unit, according to an embodiment of the present teaching.

FIG. 3*e* is an exemplar diagram of the backend unit of a special application. A backend unit may comprise a data receiving unit 350 for receiving patient data from DACMS server 102 and/or from processing sharing engine 106, a processing unit 356 for processing the received patient data, a data sending unit 352 for sending processed results to the processing sharing engine 106 and/or to a corresponding front unit of the special application. A backend unit may further include a communication unit 354 for communicating with the process sharing engine 106 and/or a frontend unit.

Figure 4:
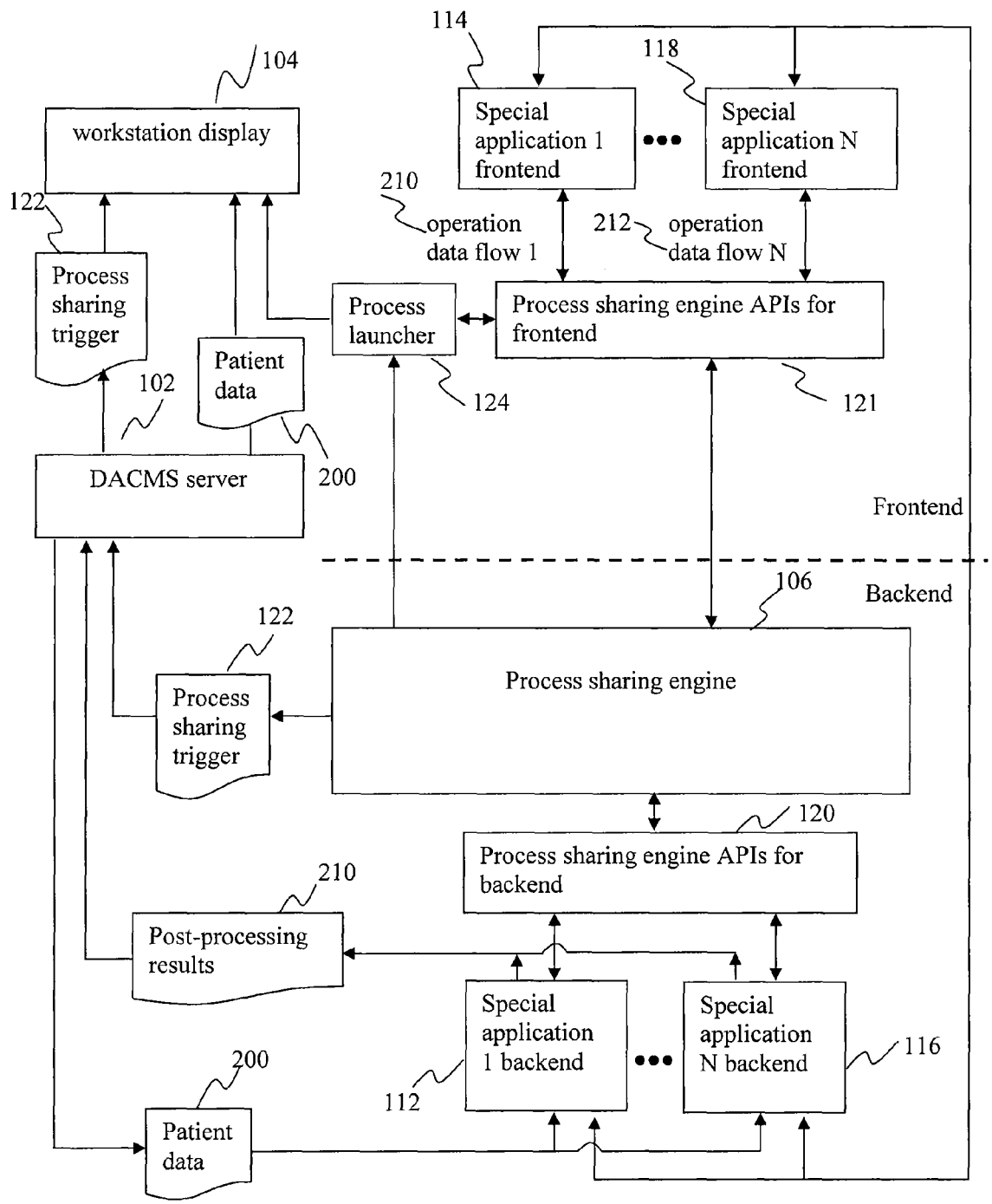
FIG. 4 shows a detailed exemplary system diagram of a process sharing engine system, according to another embodiment of the present teaching.

FIG. 4 is another system diagram of the process sharing engine system, according to another embodiment of the present teaching. In this embodiment, certain communications may occur directly between the front-end and backend of a special purpose software without having to go through a process sharing engine and the associated process sharing engine APIs for the front-end and backend. For example, in this embodiment, a special application front-end (e.g., special application front-end 118) may communicate directly with its corresponding backend (e.g., the backend component 116). This direct route of communication may be beneficial for some applications. For instance, in special applications that use graphics video streaming technology, a frontend GUI unit may need to send mouse and keyboard activities to its corresponding backend server unit to request video stream images from the backend server. Such mouse event can be transmitted or communicated faster and in a more direct manner without having to go through other layers of routing the message.

The backend component of the special application 116 may also communicate directly with the DACMS server 102. For example, the special application's backend 116 may directly obtain patient data 200 from the DACMS server 102. The special application's backend 116 may utilize the process sharing engine API for backend 120 to notify the process sharing engine 106 that particular patient data is ready to be viewed on the frontend unit 118. In some embodiments, the backend 116 may send a "ready-to-read" message to the process sharing engine 106. The special application's backend 116 may send certain configuration parameters of the server to the process sharing engine 106, so that the processing sharing engine 106 may, through the processing sharing engine API for frontend, notify the application frontend how to communicate with the backend of the application.

In those embodiments, a process sharing trigger 122 may be generated by the process sharing engine 106, corresponding to patient data 200 and one or more special application types. The process sharing trigger 122 may be generated after the preprocessing is accomplished on applications' backend components 112, . . . , 116. It may serve as an indication that the patient data 200 has been processed and available to be loaded to the frontend components of special applications 114, . . . , 118. If a special purpose software application does not have a backend unit, the process sharing trigger 122 may be automatically generated, without certain preprocessing information which may be provided by the backend components of applications.

Figure 5A:
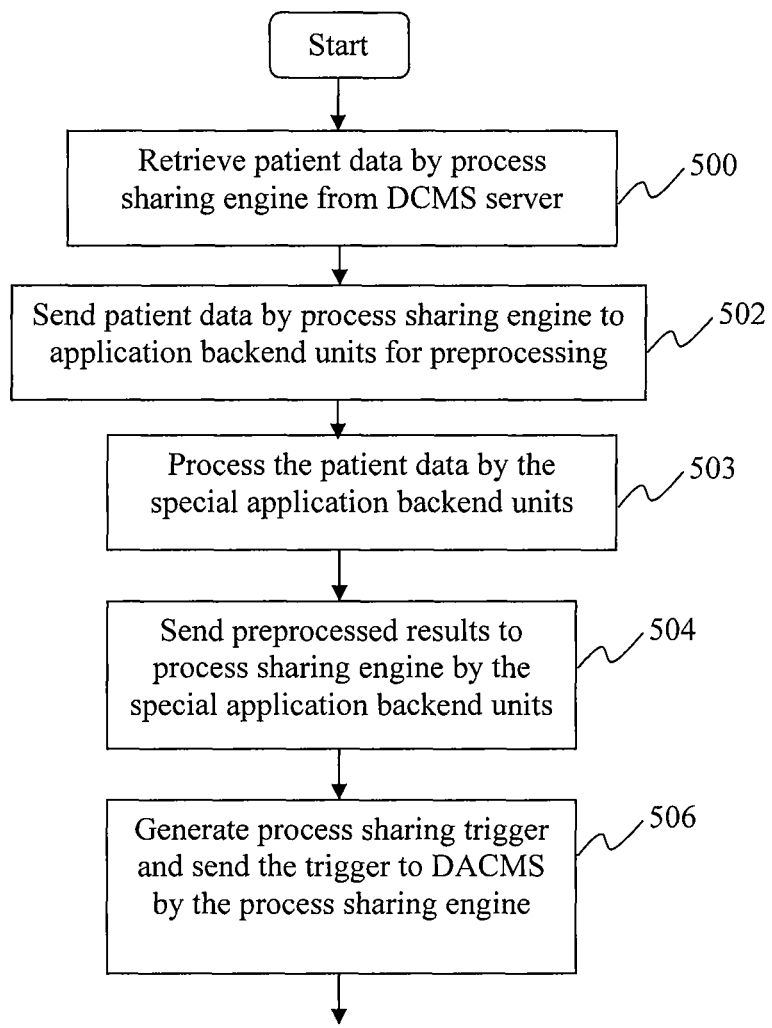
FIG. 5a is a flowchart of an exemplary backend process among a data archiving, communication and manipulation (DACMS) system, a process sharing engine and applications' backend, according to an embodiment of the present teaching.
Figure 5B:
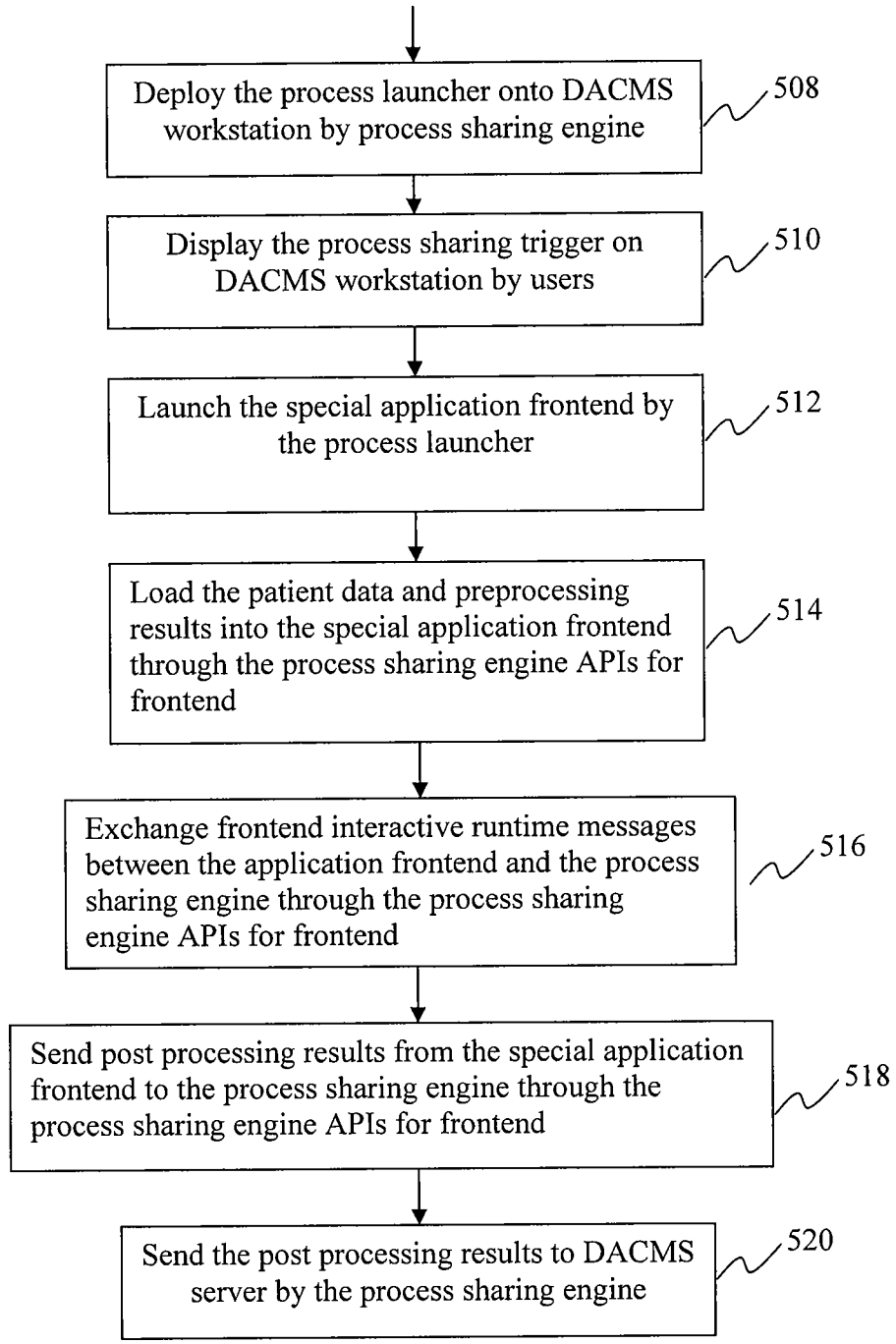
FIG. 5b is a flowchart of an exemplary front-end process among a DACMS system, a process sharing engine and applications' frontend, according to an embodiment of the present teaching.

FIG. 5*a* and FIG. 5*b* illustrate an exemplary workflow of the system corresponding to FIG. 2, in which the process sharing engine communicates with the DACMS to obtain patient data. FIG. 5*a* shows an exemplary workflow for the backend units. Patient data 200 is first retrieved by the process sharing engine 106 at step 500. Through the process sharing engine API for backend 120, the patient data is sent to the application backend unit for preprocessing at step 502. After preprocessing is done at step 503, the preprocessed results may be sent back to the process sharing engine 106 at step 504. Then a process sharing trigger 122, corresponding to the patient data 200 with respect to the application type, may be generated at step 506. The steps 502, 503, and 504 may be skipped if there is no backend unit involved for a special application.

FIG. 5b shows an exemplary flow chart for the frontend units, according an embodiment of the present teaching. First, the process launcher 124 is deployed on the DACMS workstation or installed directly in the DACMS workstation at step 508. Through a standard communication via, e.g., DICOM, the process sharing trigger may be delivered to the DACMS workstation and displayed by users at step 510. The process launcher 124 may then launch the corresponding special application's frontend program at step 512, based on the displayed trigger. Through the process sharing engine API for frontend 121, the frontend of the special application may obtain patient data and preprocessing results from the process sharing engine 106 at step 514. The process sharing engine may communicate with the frontend of the special application by sending and receiving runtime messages through the process sharing engine API for frontend 121 at step 516. Examples of the interactive runtime messages include, but not limited to, whether the frontend GUI is displayed or closed, the position and size of the GUI, and data location etc. When the reading of a study is completed, the frontend program may be put in a standby state or simply dismissed. When there are post processing results generated by the frontend, they may be sent to the process sharing engine 106 through the frontend API at step 518. In turn, the process sharing engine 106 may send the post processing results to DACMS system 101 at step 520.

Figure 6A:
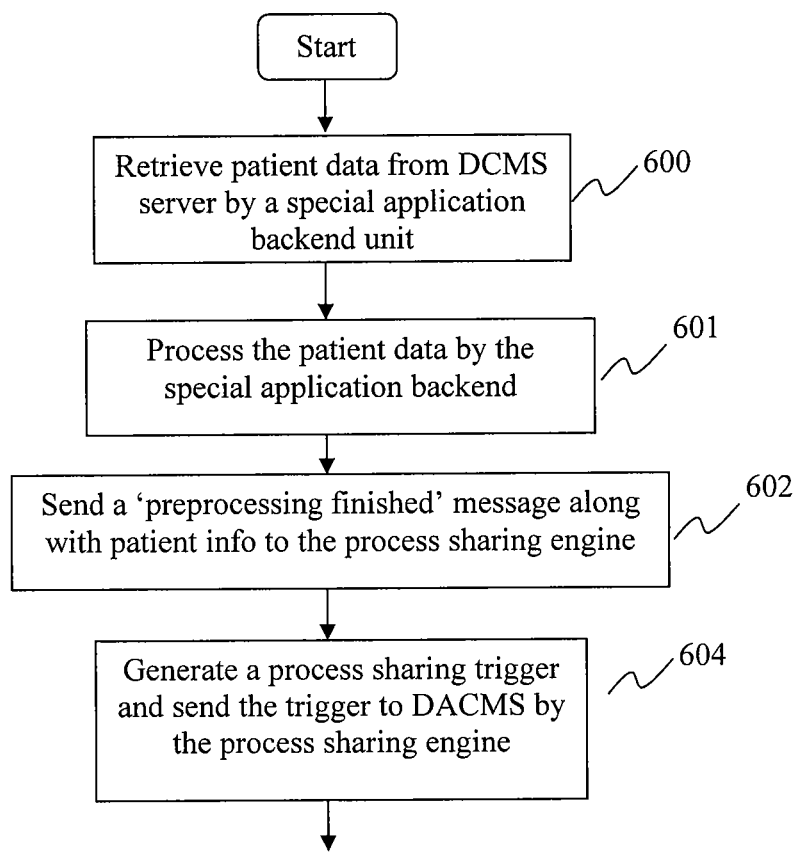
FIG. 6a is a flowchart of an exemplary backend process among a DACMS system, a process sharing engine and applications' backend, according to another embodiment of the present teaching.
Figure 6B:
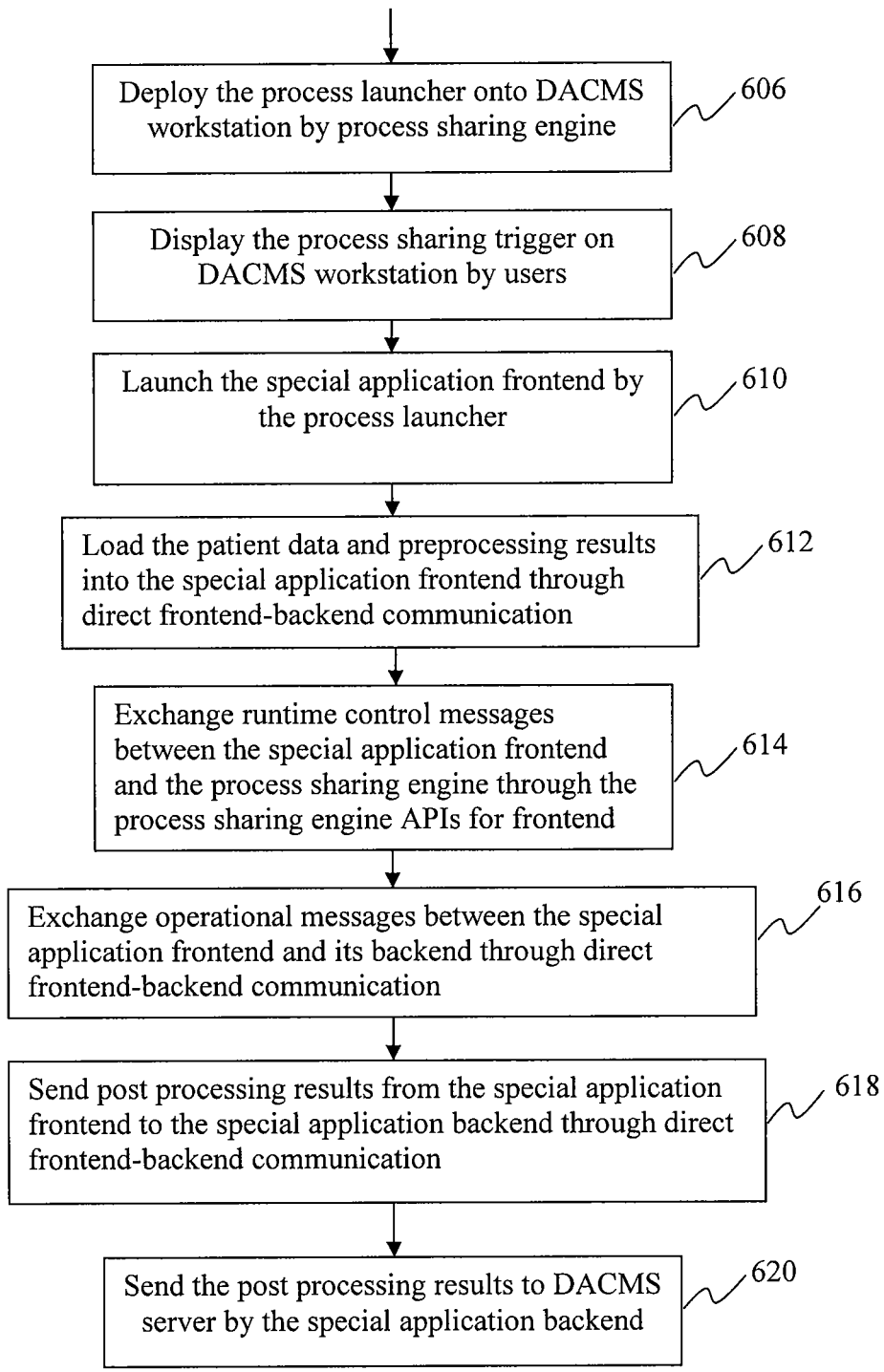
FIG. 6b is a flowchart of an exemplary frontend process among a DACMS system, a process sharing engine and applications' frontend, according to another embodiment of the present teaching.

FIG. 6a and FIG. 6b illustrate an exemplary workflow of the system corresponding to FIG. 4, in which the backend of an application communicates directly with the DACMS to obtain patient data. FIG. 6a is an exemplary workflow for the backend units. Patient data 200 is first retrieved by the application backend unit from DACMS system at step 600. At step 601, the patient data may be pre-processed by the backend units. Through the process sharing engine API for backend 120, the preprocessed results may be sent back to the process sharing engine 106 at step 602. Then a process sharing trigger 122, corresponding to the patient data 200 and the specific application type involved, is generated at step 604. The steps 600, 601, and 602 may be skipped if there is no backend unit for a special application.

FIG. 6b is an exemplary flow chart for the frontend units corresponding to FIG. 4, according to another embodiment of the present teaching. At the frontend, the process launcher 124 may be first deployed on the DACMS workstation or installed directly in the DACMS workstation at step 606. Through standard communication such as DICOM, the process sharing trigger 122 may be delivered to the DACMS workstation and displayed at step 608. The process launcher 124 may launch the corresponding special application's frontend program at step 610, based on the displayed trigger. The patient data and preprocessing results, such as server parameters, may be sent to the frontend program through direct frontend-backend communication at step 612.

The process sharing engine may communicate with the frontend of the special application by sending and receiving runtime messages through the process sharing engine API for frontend 121 at step 614. The interactive runtime messages may be similar to those illustrated in FIG. 5a. The frontend unit of the special application may communicate with its backend counterpart to operate on the patient data at step 616.

For example, in a video-streaming based rendering system, the frontend application may send mouse and keyboard activities to the backend unit. Rendered images may be video-streamed to the frontend unit and displayed to a user. When users completes a reading of a study, the frontend program may be put in a standby state or simply dismissed. Post processing results may be generated and sent directly to the application's backend at step 618. In turn, the application backend unit may send the post processing results to DACMS system at step 620.

While the inventions have been described with reference to the certain illustrated embodiments, the words that have been used herein are words of description, rather than words of limitation. Changes may be made, within the purview of the appended claims, without departing from the scope and spirit of the invention in its aspects. Although the inventions have been described herein with reference to particular structures, acts, and materials, the invention is not to be limited to the particulars disclosed, but rather can be embodied in a wide variety of forms, some of which may be quite different from those of the disclosed embodiments, and extends to all equivalent structures, acts, and, materials, such as are within the scope of the appended claims.

We claim:

1. A system for process sharing in a medical imaging system, comprising:
   a first application system capable of processing data within a second application system; and
   a process sharing engine residing outside of the second application system and configured for enabling process sharing of the first application system within the second application system based on a processed result of the data including patient data, wherein
   the first application system comprises a front-end unit that is made operable within the second application system by a process launcher upon occurrence of an event to facilitate processing of data accessible from the second application system through communication with the process sharing engine via a pre-defined interface between the process launcher and the first application system, and
   the process launcher deployed on the second application system by the process sharing engine in response to detection of a trigger at the second application system causing extraction of information associated with the first application system.

2. The system according to claim 1, wherein the process sharing engine comprises:
   a receiver configured for receiving a processing result from an application component residing outside of the second application system that processes the data accessible from the second application system
   a process sharing trigger generator configured for generating a process sharing trigger based on the data accessible from the second application system and information associated with the application component; and
   a transmission unit configured for transmit the process sharing trigger to the second application system.

3. The system according to claim 2, wherein the process sharing engine further comprises:
   a data retrieval unit configured for obtaining the data accessible from the second application system; a communication unit configured for sending the obtained data to the application component residing outside of the second application system for data processing.

4. The system according to claim 3, wherein the application component residing outside of the second application system corresponds to a backend unit of the first application system.

5. The system according to claim 1, wherein the front-end unit of the first application system comprises:
   a data receiving component configured for receiving the data accessible from the second application while operating within the second application system environment;
   a processing component configured for processing the data received from the second application system to generate a post-processing result; and a communication component capable of conducting communication with the process sharing engine.

6. The system according to claim 5, wherein the communication component of the front-end unit is further capable of communicating with a backend unit of the first application system residing outside of the second application system.

7. The system according to claim 4, wherein the backend unit of the first application system comprises:
   a data receiving component configured for receiving the data accessible from the second application system;
   a processing component configured for processing the data accessible from the second application system to generate a processed result; and
   a communication component capable of conducting communication with the process sharing engine.

8. The system according to claim 7, wherein the backend unit sends the processed result to the process sharing engine via the communication component.

9. The system according to claim 7, wherein the communication component of the backend unit is further capable of communicating with the front-end unit of the first application system operable within the second application system.

10. The system according to claim 9, wherein the backend unit sends the processed result to the front-end unit via the communication component.

11. A method for process sharing, comprising:
    obtaining data accessible from a second application system;
    sending the obtained data to an application component of a first application system for pre-processing;
    receiving a pre-processing result from the application component;
    generating a process sharing trigger based on the pre-processing result of the data including patient data and information associated with the first application system; and
    sending the process sharing trigger to the second application system, wherein
    the application component resides outside of the second application system,
    the process sharing trigger, once activated within the second application system, causes a process launcher to launch a front-end unit of the first application system within the second application system to facilitate processing of data accessible from the second application system by communicating with the process sharing engine via a pre-defined interface between the process launcher and the first application system, and
    the process launcher deployed on the second application system by the process sharing engine in response to detection of a trigger at the second application system causing extraction of information associated with the first application system.

12. The method according to claim 11, wherein the application component corresponds to a backend of the first application system.

13. The method according to claim 11, further comprising:
    detecting a presence of the process sharing trigger in the second application system;
    launching the front-end unit of the first application system within the second application system;
    loading, via the process sharing engine, the data and the pre-processing result;
    processing, by the first application system, the data accessible from the second application system environment to generate a post-processing result;
    sending the post-processing result to the second application system.

14. The method according to claim 13, wherein the processing of the data is performed by the front-end unit of the first application system.

15. The method according to claim 13, wherein the processing of the data is performed by a backend of the first application system residing outside of the second application system.

16. The method according to claim 13, wherein the sending the post-processing result is performed by the process sharing engine.

17. The method according to claim 13, wherein the detecting the presence of the process sharing trigger comprises:
    monitoring in the second application system data to be displayed; and sensing a display of the process sharing trigger.

18. A method for process sharing, comprising:
    obtaining data accessible from a second application system;
    processing the obtained data in a first application system outside of the second system to generate a pre-processing result; and
    sending the pre-processing result to a process sharing engine wherein
    the process sharing engine generates a process sharing trigger based on the pre-processing result of the data including patient data and information associated with the first application system sends the process sharing trigger to the second application system,
    the process sharing trigger, once activated in the second application system, causes a process launcher to launch a front-end unit of the first application system within the second application system to facilitate processing of data accessible from the second application system by communicating with the process sharing system via a pre-defined interface between the process launcher and the first application system, and
    the process launcher deployed on the second application system by the process sharing engine in response to detection of a trigger at the second application system causing extraction of information associated with the first application system.

19. The method according to claim 18, wherein the pre-processing result is produced by a backend of the first application system.

20. The method according to claim 18, further comprising:
    detecting a presence of the process sharing trigger in the second application system;
    launching the front-end unit of the first application system within the second application system;
    loading, via the process sharing engine, the data and the pre-processing result;
    processing, by the first application system, data accessible from the second application system environment to generate a post-processing result; sending the post-processing result to the second application system.

21. The method according to claim 20, wherein the processing of the data is performed by the front-end unit of the first application system.

22. The method according to claim 20, wherein the processing of the data is performed by a backend of the first application system residing outside of the second application system.

23. The method according to claim 20, wherein the sending the post-processing result is performed by the process sharing engine.

* * * * *